United States Patent [19]

Ajar

[11] 4,187,010

[45] Feb. 5, 1980

[54] FRAME POSITIONING APPARATUS

[76] Inventor: Charles G. Ajar, 4265 Clybourn Ave., North Hollywood, Calif. 91602

[21] Appl. No.: 838,423

[22] Filed: Sep. 30, 1977

[51] Int. Cl.² ............................................ G03B 21/46
[52] U.S. Cl. .................................................. 352/162
[58] Field of Search ........................ 352/160, 161, 162

[56] References Cited

U.S. PATENT DOCUMENTS

| 1,027,135 | 5/1912 | Leroy | 352/162 |
| 1,283,595 | 11/1918 | Taylor | 352/161 |
| 1,293,128 | 2/1919 | Larsen et al. | 352/162 |
| 1,335,749 | 4/1920 | Parkes | 352/162 |
| 1,351,814 | 9/1920 | Uhlemann | 352/161 |

*Primary Examiner*—Monroe H. Hayes
*Attorney, Agent, or Firm*—Nilsson, Robbins, Dalgarn, Berliner, Carson & Wurst

[57] ABSTRACT

An apparatus for centering each film frame within a film gate of a motion picture projector. An intermittant film pull-down mechanism is mounted on a plate which is pivotally attached to the motion picture projector body so that as the plate pivots the position of the pull-down mechanism relative to the film gate changes, thereby changing each picture frame edge respective to the film gate. A specific embodiment defines a belt driven pull-down mechanism with a drive pulley located off the plate and utilizes a rack and pinion gear as a means for pivoting the plate.

3 Claims, 7 Drawing Figures

FRAME POSITIONING APPARATUS

FIELD OF THE INVENTION

The invention relates to motion picture film frame positioning apparatus.

BACKGROUND AND SUMMARY OF THE INVENTION

Methods and apparatus to change the position of a film frame in a motion picture projector film gate are many and varied. Most utilize sophisticated mechanical gearing and linkage arrangements which are difficult to maintain, require frequent cleaning and adjustment and add to the noise of the projector. There has long been a need for a simple, reliable apparatus to adjust film framing in a film gate.

The apparatus disclosed herein provides for simple, reliable and quiet film frame adjustment. A mechanism for intermittently pulling down film through a motion picture projector film gate, such as a Geneva mechanism, is mounted on a moveable plate so that the pull-down mechanism can be moved relative to the film gate. By such means, the position of engagement and release of the film sprocket holes changes with respect to the film gate, so that the centering of each film frame can be appropriately adjusted.

In a particular embodiment, a somewhat elongated plate is utilized with one end pivotally mounted to the motion picture projector body and the film engaging portions of the pull-down mechanism mounted near the other end. A rack is also attached at the other end which, in conjunction with a pinion gear, is used to pivot the plate about its pivot point, thereby changing the position of the pull-down mechanism relative to the film gate. The pull-down mechanism is operatively connected to a pulley located on the other side of the plate which is driven by a belt which in turn is driven by a drive pulley located off the plate. Although spring loaded mechanical gearing could be used to drive the pull-down mechanism, the belt driven embodiment described above provides a particularly easy way to change the position of the pull-down mechanism pulley with respect to the drive pulley without having to provide for gear interface adjustments.

A further embodiment provides for the drive pulley to also drive rotating film carriage sprockets located above and below the film gate. During normal projection, a film loop is provided between the upper sprocket and the film gate thereby providing the slack necessary for each intermittent pull-down cycle. If film direction is reversed, the upper sprocket pulls the film upward through the film gate and another film loop is formed between the pull-down mechanism and the film gate. The belt driven upper sprocket provides a continuous pulling of the film through the film gate, thus eliminating film breakage often experienced when the upper sprocket acts only as an idler gear and the pull-down mechanism itself is used to push the film upwardly through the film gate.

DETAILED DESCRIPTION

As required, a detailed illustrative embodiment of the invention is disclosed herein. This embodiment exemplifies the invention and is currently considered to be the best embodiment for such purposes. However, it is to be recognized that details of the pull-down mechanism may be somewhat different from those disclosed. Accordingly, the specific structural details disclosed are representative and provide the basis for the claims which define the scope of the present invention.

As above indicated, the invention discloses an apparatus for positioning a film frame within a motion picture film gate. The apparatus consists of a slightly elongated plate one end of which is pivotally mounted to the motion picture projector body, and a film pull-down mechanism, which can be a Geneva mechanism, mounted at the other end to which is also mounted a rack which mates with a pinion gear rotatably mounted to the projector body. The pull-down mechanism is operatively connected to a belt driven pulley, the belt being connected to a drive mechanism mounted off the elongated plate. The drive mechanism, through appropriate belts and pulleys, also drives an upper and lower film carriage sprocket positioned relative to the film gate.

Figure 1:
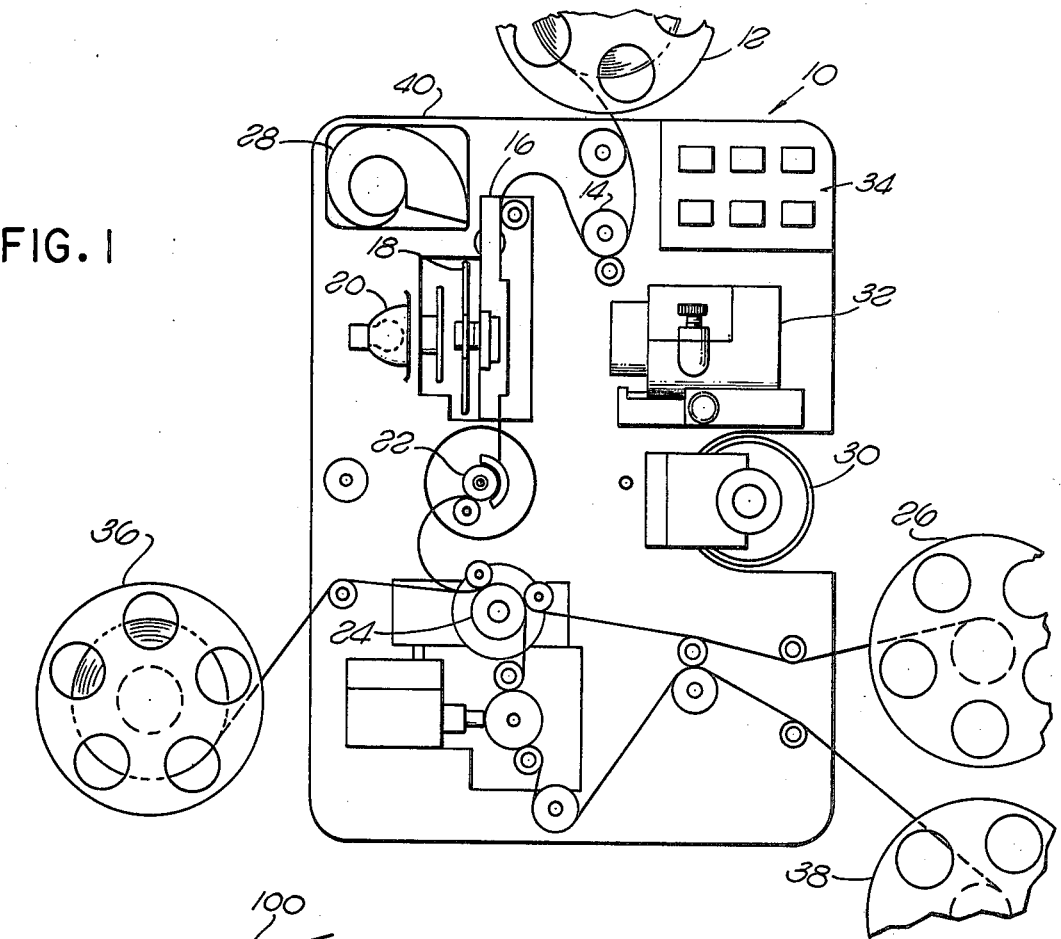
FIG. 1 is an elevational view of one side of a motion picture projector incorporating an apparatus of the present invention.

The supportive and operative elements of the invention can be seen in FIG. 1. A motion picture projector 10 is shown having a film supply reel 12, upper sprocket 14, film gate 16, shutter 18, light source 20, film pull-down mechanism 22, lower sprocket 24, film take-up reel 26, cool air blower 28, drive motor 30, lens assembly and positioner 32 and control panel 34. In addition, a sound track supply reel 36 and sound track take-up reel 38 are shown. The projector 10 has a vertical partition 40 which divides the projector lengthwise into two sides. The film gate 16, upper sprocket 14, pull down mechanism 22 and lower sprocket 24 have their operative surfaces extending into one side of the film projector first portion and their associated drive mechanisms extending into the other side as shown in FIG. 4.

Figure 4:
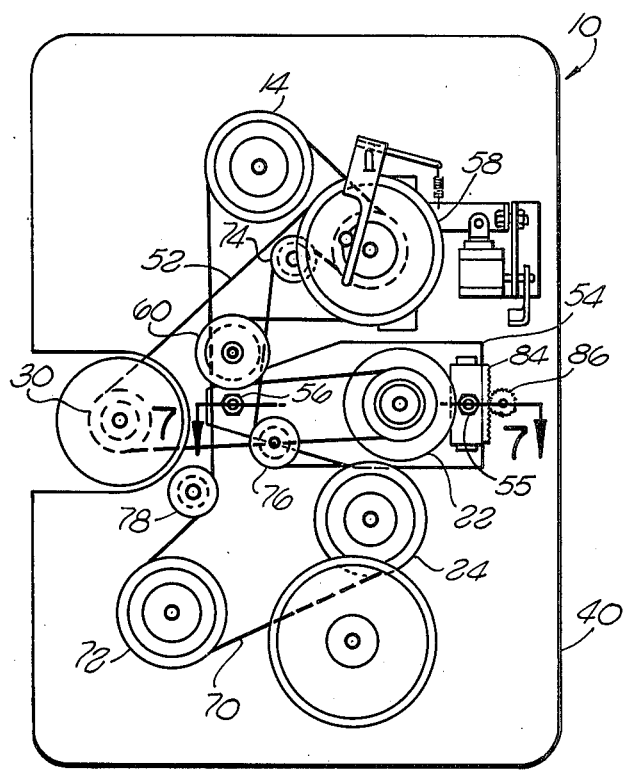
FIG. 4 is an elevational view of the other side of the motion picture projector showing the apparatus of the present invention and the pulley/belt system used to drive the upper and lower sprockets and the pull-down mechanism.

Referring to FIG. 4, the pulley/belt configuration for driving the motion picture projector 10 is shown for reasons which will be explained below. A drive motor 30 drives a first belt 52, shown in detail in FIG. 5, which in turn drives the film pull-down mechanism 22 which is mounted on a plate 54, one end of which is pivotally attached to the vertical partition 40 through a pivot 56. The first belt also drives a shutter rotation and fire shield centrifugal clutch 58, the operation of which is unimportant for the purposes of the present invention. An idler pulley 60 is used to conveniently route the first belt 52.

Figure 6:
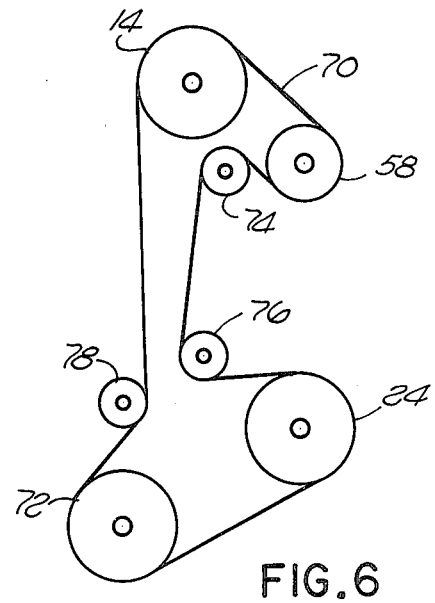
FIG. 6 is a schematic view showing the second belt and its interfacing pulleys.

A second belt 70, shown schematically in FIG. 6 is driven by a pulley formed as part of the centrifugal clutch 58 and drives the upper sprocket 14, the lower sprocket 24 and a sound track sprocket 72. Three idler gears 74, 76 and 78 are provided for convenient routing of the second belt 70.

Figure 7:
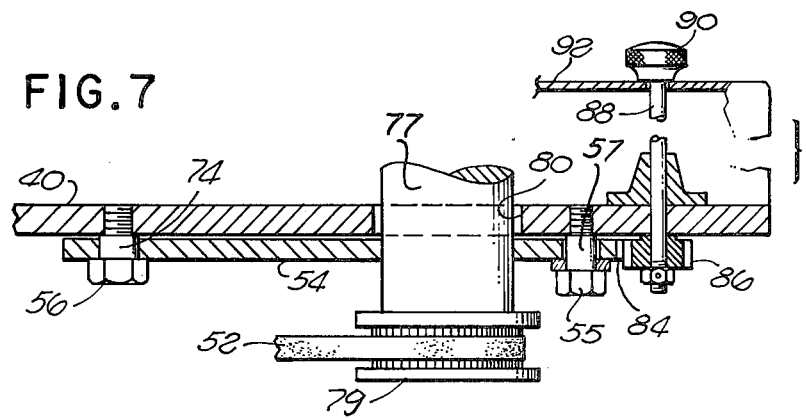
FIG. 7 is a cross-sectional view taken along line 7—7 of FIG. 4 showing the pull-down mechanism mounting plate and the rack and pinion gear for the positioning thereof.

The plate 54 on which the pull-down mechanism 22 is mounted can be seen in FIG. 7. The pivot consists of a bolt 56 mounted in the projector partition 40 and extends through a hole 74 formed in one end of the mounting plate. A shaft 77 connects the pull-down mechanism 22 on one side of the partition 40 with its associated drive pulley 79 on the other side of the partition 40. A vertically extending aperture 80 is formed in the partition 40 so that the connecting shaft 77 can freely move as the plate 54 pivots. Pivoting is controlled by a rack 84 mounted at the other end of the plate 54 to the partition 40 by a bolt 55 extending through an elongate slot 57 and a pinion gear 86 which is connected via a shaft 88 extending through the partition 40 to a knob 90 positioned external to the projector case 92 for ease of adjustment.

Figure 5:
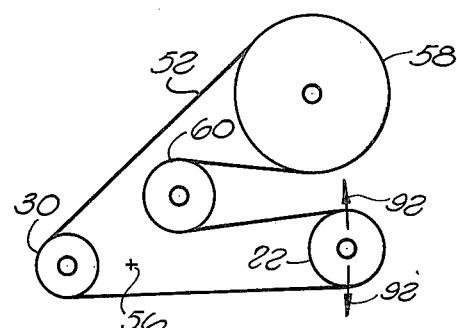
FIG. 5 is a schematic view showing the first belt and its interfacing pulleys.

In operation, one can appreciate that as the pinion gear 86 is rotated, the position of the pull-down mechanism 22 relative to the film gate 16 changes as the mounting plate 54 rotates about the pivot bolt 56. As can be seen in FIG. 5, the rotation of the pull-down mechanism 22 in relation to the fixed drive motor 30 can be readily accommodated by the drive belt 52.

Figure 2:
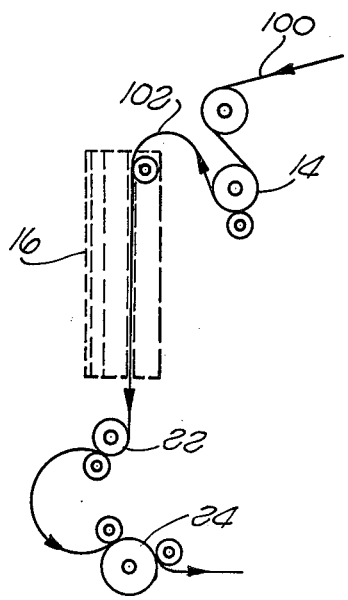
FIG. 2 is a schematic of a film strip passing through the projector of FIG. 1 in a forward direction.
Figure 3:
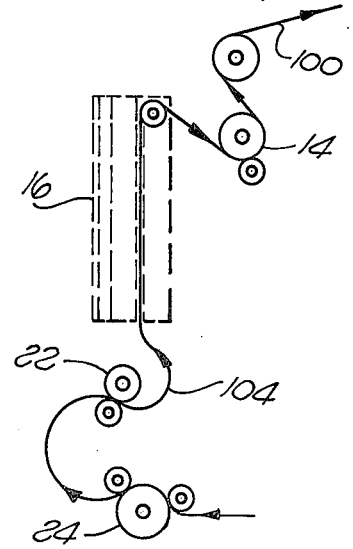
FIG. 3 is a schematic of a film strip passing through the projector of FIG. 1 in a reverse direction.

A second advantage of the belt driven configuration herein disclosed is the elimination of film breakage as film direction is reversed. In many motion picture projectors, film reversal is effected by the pull-down mechanism 22 pushing the film upward through the film gate 16 which frequently causes breakage or crumpling of the film. However, as above indicated, with the apparatus disclosed herein, the upper sprocket 14, pull-down mechanism 22 and lower sprocket 24 are driven by the drive motor 30 and are operatively coupled to each other by the first and second drive belts 52 and 70. Accordingly, film reversal is effected by the belt-driven upper sprocket reversing direction. Referring to FIG. 2, the film is routed around the upper sprocket 14 and forms a first loop 102 prior to entering the film gate 16. It is this first loop 102 that forms slack which compensates for the difference between the constant rotation of the upper sprocket 14 and intermittent pull-down action of the pull-down mechanism 22. Referring to FIG. 3, as the upper sprocket 14 takes up the film slack from the first loop 102, the pull-down mechanism 22, which has also reversed direction, forms a second film loop 104 between itself and the entrance to the film gate 16. Again it is this second loop 104, which was formed due to the inherent characteristics of the above-described configuration, which supplies the compensation for the difference between the constant rotation of the upper spindle 14 and the intermittent pushing action of the pull-down mechanism 22. Thus the film 100 is pulled at a constant speed through the film gate 16 by the upper sprocket 14.

I claim:

1. In a motion picture projector having a film gate, upper and lower sprockets relative to said film gate, a mechanism for intermittently pulling down said film through said gate and a means for having each film frame centered within said gate at the completion of each intermittent pull-down cycle, the improvement according to which said centering means comprises:

a plate having first and second opposite sides;

said intermittent pull-down mechanism having film engaging portions mounted on the first side of said plate and a first pulley connected thereto on the second side of said plate;

a belt for driving said first pulley;

a drive pulley located off one end of said plate for driving said belt;

a pivot for said plate aligned with and between said drive pulley and said first pulley; and means for rotating said plate about said pivot so that said pull-down mechanism is moved relative to said gate whereby centering of said frames can be adjusted.

2. The improvement of claim 1 wherein said means for rotating said plate is a rack and pinion gear said rack and pivot being disposed on an end of said plate opposite said one end whereby rotation of said pinion causes said plate to rotate.

3. The improvement of claim 1 including means driven by said drive pulley for driving said upper and lower sprockets whereby a film loop is formed by said film prior to entering said film gate regardless of the direction of travel of said film.

* * * * *